United States Patent
Hedmann et al.

(10) Patent No.: US 10,525,185 B2
(45) Date of Patent: Jan. 7, 2020

(54) METHOD OF DETERMINING A SYSTEM COMPRESSIBILITY VALUE OF A MEDICAL MEMBRANE PUMP DRIVE

(71) Applicant: FRESENIUS MEDICAL CARE DEUTSCHLAND GMBH, Bad Homburg (DE)

(72) Inventors: Frank Hedmann, Volkach (DE); Torsten Hochrein, Eschenau (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 151 days.

(21) Appl. No.: 15/509,009

(22) PCT Filed: Sep. 3, 2015

(86) PCT No.: PCT/EP2015/001782
§ 371 (c)(1),
(2) Date: Mar. 6, 2017

(87) PCT Pub. No.: WO2016/034286
PCT Pub. Date: Mar. 10, 2016

(65) Prior Publication Data
US 2017/0290971 A1    Oct. 12, 2017

(30) Foreign Application Priority Data
Sep. 4, 2014   (DE) .......... 10 2014 013 152

(51) Int. Cl.
*A61M 1/00*   (2006.01)
*A61M 1/28*   (2006.01)
(Continued)

(52) U.S. Cl.
CPC .......... *A61M 1/281* (2014.02); *A61M 1/3626* (2013.01); *F04B 43/067* (2013.01); *A61M 2205/3331* (2013.01)

(58) Field of Classification Search
CPC ........ A61M 1/1037; A61M 1/14; A61M 1/28; A61M 2005/14513; A61M 2205/12; A61M 2205/3331; A61M 5/1413; A61M 5/14593; A61M 5/36; A61M 1/106; F04B 43/067; F04B 51/00; F04B 43/00
See application file for complete search history.

(56) References Cited

U.S. PATENT DOCUMENTS

2011/0185722 A1* 8/2011 Sebesta .................. A61M 1/14
60/527
2012/0302945 A1* 11/2012 Hedmann ......... A61M 5/16809
604/29

FOREIGN PATENT DOCUMENTS

CN   102725007   10/2012
CN   103443610   12/2013
(Continued)

*Primary Examiner* — Rebecca E Eisenberg
(74) *Attorney, Agent, or Firm* — Jacobson Holman, PLLc.

(57) ABSTRACT

A method of determining a system compressibility value of a medical membrane pump drive is provided which includes moving to a first and second pressure level and detecting a first and second operating parameter value of the membrane pump drive. The system compressibility value is determined on the basis of the detected operating parameter values and the membrane of the membrane pump drive is supported at a rigid surface during the determination of the system compressibility value.

17 Claims, 3 Drawing Sheets

(51) Int. Cl.
*F04B 43/067* (2006.01)
*A61M 1/36* (2006.01)

(56) References Cited

FOREIGN PATENT DOCUMENTS

| | | |
|---|---|---|
| DE | 19919572 | 11/2000 |
| DE | 102011105824 | 5/2012 |
| WO | WO 2013/176770 | 11/2013 |

\* cited by examiner

METHOD OF DETERMINING A SYSTEM COMPRESSIBILITY VALUE OF A MEDICAL MEMBRANE PUMP DRIVE

BACKGROUND OF THE INVENTION

1. Field of the Invention

The present invention relates to a method of determining a system compressibility value of a medical membrane pump drive as well as to a method of determining an air proportion and/or an air quantity in a medical fluid conveyed by a membrane pump.

Membrane pumps are frequently used in the field of medical engineering, and in particular in the field of dialysis technology, to pump medical fluids such as dialyzate or blood. In this respect, a membrane pump typically has a pump chamber closed by a membrane, wherein fluid can be pressed out of the pump chamber by pressing the membrane into the pump chamber and fluid can be sucked into the pump chamber by pulling the membrane out of the pump chamber. Fluid can hereby be pumped through the pump chamber in interaction with corresponding valves.

The pump chamber is in this respect mostly arranged in a disposable, for example in a pump cassette, that is coupled to a membrane pump drive. The membrane pump drive in this respect typically has a drive chamber that is likewise closed by a membrane. The pump chamber and the drive chamber are then coupled to one another such that the membrane of the pump chamber follows the movement of the membrane of the drive chamber.

With a piston membrane pump, the drive chamber is in this respect in hydraulic communication with a piston-in-cylinder unit. Hydraulic fluid can be pressed into or sucked out of the drive chamber by moving the piston, which has the consequence of a corresponding movement of the membrane of the drive chamber. Such an arrangement has the advantage that the pump pressure can be controlled by a corresponding control or regulation of the pressure in the hydraulic part. Furthermore, membrane pumps allow a simple balancing of the pumped fluids since the volume change of the pump chamber and thus the fluid displacement on a pump stroke corresponds to the volume change of the control chamber (with the opposite sign), wherein this can be determined exactly via the position of the piston of the piston-in-cylinder unit.

Error sources can, however, occur here. On the one hand, air collected in the pump chamber can have the result that the fluid quantity pumped through the pump chamber does not exactly correspond to the volume change of the drive chamber. Furthermore, due to a certain system compressibility of the membrane pump drive, the volume change of the control chamber can differ from the volume change caused by the movement of the piston of the piston-in-cylinder unit. In this respect, air that collects in the hydraulic fluid can in particular result in a certain compressibility of the hydraulic system. Furthermore, hoses that connect the piston-in-cylinder unit to the drive chamber can, for example, have a certain flexibility and therefore expand at an elevated pressure. A certain system compressibility that influences the values detected for the balancing can also occur with other drive mechanisms.

2. Description of the Related Art

A method is in this respect known from DE 19919572 A1 by which the air proportion can be determined in the fluid pumped through a pump chamber. For this purpose, the pump chamber is first filled by gravity and the starting pressure hereby resulting is measured. The cut-off valves of the pump chamber are thereupon closed so that a fluid volume enclosed therein results. With closed cut-off valves, the piston-in-cylinder unit is then actuated to act on the closed fluid volume with a predefined end pressure. The volume change of the fluid volume in the pump chamber accompanying this pressure change in this respect directly depends on the proportion of air in the enclosed fluid volume. The air proportion can therefore be determined with the aid of the volume change that is produced by the pressure difference and that is determined via the piston movement. In this respect, in DE 19919572 A1, the influence of the system compressibility of the membrane pump drive is taken into account by a fixedly predefined constant. However, the system compressibility can, for example, vary due to air collecting in the hydraulic fluid during the operation of the pump, which remains out of consideration in DE 19919572 A1.

A method is therefore known from DE 102011105824 B3 how the system compressibility of a membrane pump drive can be determined. In this respect, the system compressibility of the pump apparatus filled with gas is determined in that a start pressure and an end pressure are adjusted using a pressure sensor and the associated pump positions or pump sensor values are recorded. The spring constant which is set as equivalent to the system compressibility is determined on the basis of the value pairs.

SUMMARY OF THE INVENTION

In accordance with a first aspect, it is the object of the present invention to provide an improved method of determining a system compressibility of a medical membrane pump drive. In accordance with a second aspect, it is the object of the present invention to provide an improved method of determining an air proportion and/or an air quantity in a medical fluid conveyed by a membrane pump. It is furthermore the object of the present invention to provide corresponding membrane pump drives or blood treatment machines having corresponding membrane pump drives that carry out the methods in accordance with the invention.

In accordance with the first aspect, the present invention comprises a method of determining a system compressibility value of a medical membrane pump drive in which a first and a second pressure level are moved to and a first and second operating parameter value of the membrane pump drive is detected, with the system compressibility value being determined on the basis of the detected operating parameter values. In accordance with the present invention, the membrane of the membrane pump drive is in this respect supported at a rigid surface during the determination of the system compressibility value. The membrane of the membrane pump drive can in particular be supported at a rigid surface in this respect while the first and second operating parameter values corresponding to the first and second pressure levels are detected.

The present invention in this respect takes into account that a membrane pump drive actually does not represent a closed system whose total volume is unchangeable, but is rather coupled to further system parts by the membrane of the membrane pump drive. Since the membrane of the membrane pump drive is supported at a rigid surface in accordance with the invention during the determination of the system compressibility, the system compressibility of the membrane pump drive can, however, be largely sealed off from external influences. The system compressibility value determined in accordance with the invention therefore more exactly reproduces the compressibility going back to the membrane pump drive itself. Furthermore, the determination in accordance with the invention is no longer influenced by the counter-pressure of the membrane of the membrane pump drive.

The system compressibility value in accordance with the invention can in this respect be any desired parameter by which a compressibility property or the yielding of the membrane pump drive on pressure changes can be characterized and preferably quantified. In this respect, the membrane pump drive positions associated with the first and second pressure levels are used as the operating parameter values from which the system compressibility value is calculated.

To move to the first and second pressure levels, the membrane pump drive is preferably actuated until the pressure of the membrane pump and/or of the membrane pump drive reaches the first pressure level. The first operating parameter value of the membrane pump drive is thereupon determined. The membrane pump drive is then actuated until the pressure of the membrane pump and/or of the membrane pump drive reaches the second pressure level and then the second operating parameter value is determined. The pressure of the membrane pump drive and/or of the membrane pump can in this respect be detected via a pressure sensor. The operating parameter can be determined via a corresponding operating parameter sensor, for example via a position sensor and/or a motion sensor.

The first and second pressure levels can in this respect be predefined pressure levels. They can in particular be stored in a control of the membrane pump drive.

In accordance with a preferred embodiment of the present invention, the first and second pressure levels at which the operating parameter values are determined exceed the maximum counter-pressure of the membrane of the membrane pump drive. This provides that, depending on whether work is being done at a vacuum or at excess pressure, the membrane is either deflected outwardly or inwardly by a maximum while the respective operating parameter value present at the first and second pressure levels is determined.

The method in accordance with the invention is preferably used with those system in which a pump cassette having a pump chamber arranged therein is couplable to the membrane pump drive.

In accordance with a first variant of the present invention, the determination of the system compressibility value can take place in this respect before the pump. cassette is coupled. The membrane in this case preferably contacts a receiving surface of a pump cassette receiver during the determination of the system compressibility value. Such a pump cassette receiver is in this respect used in normal pump operation to hold the pump cassette at the coupling surface of the membrane pump drive. For this purpose, it has a receiving surface at which the rear wall of the pump chamber is supported in the inserted state of the pump cassette. In accordance with the present invention, the determination of the system compressibility value can now take place before the pump cassette has been inserted, with the membrane in this respect contacting this receiving surface. The receiving surface can in this respect, for example, approximately follow the shape of the pump chamber and typically has a concave shape.

In a second variant of the present invention, the determination of the system compressibility value can take place with a coupled pump cassette. In this respect, the membrane of the membrane pump drive can be completely pressed into the pump chamber of the pump cassette during the determination of the system compressibility value and can be supported at the rear wall of the pump chamber. The membrane of the membrane pump drive in this state contacts the membrane of the pump cassette that in turn contacts the rear wall of the pump chamber.

The determination of the system compressibility value preferably takes place at excess pressure in the two above-described variants. The membrane of the membrane pump drive is hereby pressed out of a drive chamber toward the corresponding counter-surface.

The determination of the system compressibility value can, however, also take place by applying a vacuum. The membrane is in this respect preferably drawn completely into the drive chamber of the membrane pump drive and contacts a rear wall of this drive chamber. The influence of further components on the determination of the system compressibility value of the membrane pump drive can hereby also be reduced or avoided.

The present invention can in particular be used in such membrane pump drives in which, in normal operation, the pump cassette is pressed toward a coupling surface of the membrane pump drive by the pressurizing of an air cushion arranged behind the pump cassette. A pump cassette receiver into which the pump cassette is inserted in normal operation can in this respect in particular be moved together with the pump cassette toward the coupling surface of the membrane pump drive due to the filling of the air cushion.

The determination of the system compressibility value in this respect preferably takes place after the air cushion has been filled to operating pressure. This is of advantage independently of whether the system compressibility value is determined with or without an inserted pump cassette since it is ensured by the filling of the air cushion that the counter-surface the membrane contacts does not move. A mechanical clearance that is present without the pressing on and a mechanical deformation is in particular hereby reduced or avoided during the measurement. The operating pressure of the air cushion is in this respect preferably greater than the first and second pressure levels and/or the force exerted onto the pump cassette receiver by the air cushion is greater than the force exerted by the first and second pressure levels via the membrane of the membrane pump drive such that the exact level of the operating pressure has no influence on the determination of the system compressibility.

The determination of the system compressibility at vacuum can in this respect take place both with an inserted pump cassette and before the insertion of the pump cassette.

If the determination of the system compressibility value takes place with an inserted cassette, at least one valve of the pump chamber is preferably open to allow a fluid flow into or out of the pump chamber when the membrane contacts the rear wall of the drive chamber or of the pump chamber on the moving to the first operating pressure.

The first pressure level used in accordance with the invention is preferably greater than 50 mbar since the typically used membranes typically generate a counter-pressure of approximately 50 mbar. The first pressure level is preferably greater than 75 mar, further preferably greater than 100 mbar, and further preferably greater than 150 mbar. It is hereby ensured that the membrane is completely laid against the counter-surface on the reaching of the first pressure level. The first pressure level is, however, preferably less than 600 mbar. It is hereby ensured that the system compressibility value is measured in a pressure range that also occurs in the normal pump operation of the pump. The first pressure level is in this respect preferably smaller than 400 mbar, further preferably smaller than 300 mbar, and further preferably smaller than 250 mbar. A certain pressure value range above the first pressure level is hereby still provided to move to the second pressure level.

The second pressure level is preferably likewise greater than 50 mbar, further preferably greater than 200 mbar, further preferably greater than 250 mbar. It is hereby achieved that the membrane is fully placed on. The second pressure level is in this respect preferably higher than the first pressure level. The second pressure level is, however, preferably smaller than 600 mbar, preferably smaller than 500 mbar, further preferably smaller than 450 mbar, further preferably smaller than 400 mbar. The measurement range for the determination of the system compressibility value is hereby held in a pressure range that is also reached in normal pump operation.

The above-indicated pressure values are in this respect indicated as absolute values of the pressure difference via the membrane, i.e. the pressure difference between the pressure in the drive chamber and the pressure that is applied at the outer surface of the membrane. It can therefore be an excess pressure or a vacuum at the indicated level. In this respect, atmospheric pressure is preferably applied at the outer surface of the membrane while the system compressibility value is determined.

The difference between the first and second pressure levels is further preferably greater than 5 mbar, further preferably greater than 10 mbar, further preferably greater than 40 mbar, further preferably greater than 80 mbar. A certain precision in the determination of the system compressibility value is ensured by a sufficiently large pressure difference between the first and second pressure levels. If, in contrast, the pressure difference is selected as too small, it only corresponds to a minimal change of the pump drive position, which increases the influence of measurement errors.

The difference between the first and second pressure levels, however, is preferably smaller than 500 mbar, preferably smaller than 400 mbar, further preferably smaller than 300 mbar, further preferably smaller than 200 mbar. Pressure levels can hereby be selected that are in the normal operating range of the pump drive during pumping. The measurement can furthermore take place fast.

For example, the first pressure level can amount to approximately 200 mbar and the second pressure level to approximately 300 mbar.

Provision can be made in accordance with the method in accordance with the invention that a system compressibility value is determined both at vacuum and at excess pressure. Effects can hereby be taken into account that have different effects on the system compressibility value at vacuum and at excess pressure.

As already presented above, any desired parameter can be determined as the system compressibility value that is correlated with the yielding of the pump drive on a pressure change. The system compressibility value in this respect particularly preferably depends on the difference of the operating parameter values that are determined at the first and second pressure levels. The system compressibility value is in this respect in particular determined using this difference.

The system compressibility value in this respect preferably depends on the difference between the pump positions that the membrane pump drive adopts at the first and second pressure levels. The system compressibility value can in particular be simply determined as this difference.

The method in accordance with the invention is preferably used with a membrane pump drive that has a drive chamber that is closed by the membrane, with the membrane being deflected outwardly out of the drive chamber by excess pressure in the drive chamber and being deflected inwardly into the drive chamber by a vacuum in the drive chamber.

The membrane pump drive can furthermore have a pressure sensor that determines the pressure in the drive chamber to move to the first and second pressure levels.

The pressure in the drive chamber can furthermore preferably be produced via a piston-in-cylinder unit in communication with the drive chamber. The piston-in-cylinder unit can in this respect in particular be in fluid communication with the drive chamber, for example via a connection hose. A length sensor is further preferably provided that detects the position of the piston as an operating parameter value.

The transmission of the pressure onto the membrane preferably takes place hydraulically. The piston-in-cylinder unit and the working chamber can in particular be hydraulically connected to one another.

As already stated above, the main factors of influence for the system compressibility with such an embodiment of the membrane pump drive as a piston membrane pump are the air that has collected in the hydraulic fluid of the hydraulic system and the yielding of the connection hose between the piston-in-cylinder unit and the drive chamber. This system compressibility can now be determined in accordance with the invention without external values falsifying the measured value via the membrane.

The present invention further comprises a membrane pump drive having a pressure sensor and having a control, wherein the control has a function for carrying out a method in accordance with the invention such as was described above. The function can in this respect in particular automatically determine the system compressibility value of the membrane pump drive. The control can move to the first and second pressure levels for this purpose and can detect the associated first and second membrane pump drive values, with the pressure levels being selected such that the membrane is supported on a rigid surface.

The determination of the system compressibility value in this respect in particular takes place in the activation phase, i.e. before the actual pump operation. The function in accordance with the invention can in this respect be integrated into the activation routine. The function in accordance with the invention can in this respect in particular carry out the determination of the system compressibility value in an automated manner as part of the activation routine and/or in response to a user input.

The membrane pump drive preferably furthermore has a sensor for determining an operating parameter value, in particular a position sensor for determining a membrane pump drive position.

The membrane pump drive furthermore preferably has a coupling surface to which a pump cassette can be coupled.

The membrane pump drive is in this respect preferably designed such as was already presented in more detail above with respect to the method in accordance with the invention. It is in particular the drive of a piston membrane pump. The function furthermore preferably carries out the method in accordance with the invention such as has already been presented above.

The present invention furthermore comprises a blood treatment machine, in particular a dialysis machine, in particular a peritoneal dialysis machine, having such a membrane pump drive. The blood treatment machine in this respect in particular has a pump cassette receiver and/or an air cushion for pressing the pump cassette toward a coupling surface of the membrane pump drive. The control of the membrane pump drive is in this respect preferably integrated into the control of the blood treatment machine such that it has a function for carrying out the method in accordance with the invention.

In accordance with a second aspect, the present invention comprises a method for determining an air proportion and/or an air quantity in a medical fluid conveyed by a membrane pump. For this purpose, a first and a second pressure level are moved to by a corresponding control of a membrane pump drive of the membrane pump and associated operating parameter values of the membrane pump are detected, with the air proportion and/or the air quantity being determined on the basis of the operating parameter values. Unlike in accordance with the methods known from documents DE 19919572 A1 and DE 102011105824 B3, it is thus not the pressure level randomly resulting from the gravity filling of the pump chamber that is used as the starting pressure as the first pressure level, but rather a predefined pressure level moved to by a corresponding control of the membrane pump drive. The determination of the air proportion or of the air quantity is hereby independent of the pressure being randomly adopted in the pressure chamber during the gravity filling.

The determination of the air proportion and/or of the air quantity preferably takes place in that all the valves of the pump chamber are closed after the filling of the pump chamber such that a closed fluid volume within the pump chamber results. The first pressure level is thereupon first moved to and the first operating parameter value is determined by a corresponding control of the membrane pump drive and then the second pressure level is moved to and the associated second operating parameter value is determined by a repeat control of the membrane pump drive. The air proportion and/or the air quantity can in this respect preferably be determined with reference to the first and second pressure levels as well as to the first and second operating parameter values.

A pump position is in this respect preferably determined as the operating parameter value. The position of the piston of the piston-in-cylinder unit can in particular be determined as the operating parameter value for this purpose with a piston membrane pump.

The calculation of the air proportion and/or of the air quantity can then take place in accordance with the formula already known from DE 19919572 A1.

The method in accordance with the invention is in this respect preferably used such as has already been described above in detail with respect to the first aspect. It can in particular be a piston membrane pump. The method in accordance with the invention can in this respect, however, be used independently of the determination of a system compressibility value presented there.

However, a system compressibility value of the membrane pump drive is preferably taken into account in the determination of the air proportion and/or of the air quantity in accordance with the second aspect. The accuracy in the determination of the air proportion and/or of the air quantity is hereby increased.

In this respect, a third and fourth pressure level are preferably moved to and associated operating parameter values of the pump are detected for determining the system compressibility value, with the system compressibility value being determined on the basis of the operating parameter values. The operating parameter vales can in turn be operating parameter values that are used for determining the air proportion and/or air quantity. The determination of the system compressibility value in this respect preferably takes place in the activation phase of the membrane pump.

The same two pressure levels that are also used in the determination of the air proportion and/or the air quantity are preferably used in the determination of the system compressibility value. This has the great advantage that the system compressibility value does not have to be determined for a plurality of pressure levels or pressure changes, but only for the first and second pressure levels and that nevertheless correctly reproduces the proportion of the system compressibility in the values measured in the determination of the air proportion and/or air quantity. This procedure is in this respect only made possible by the method in accordance with the invention for determining the air proportion and/or the air quantity in accordance with the second aspect of the present invention according to which the first and second pressure levels are actively moved to such that two predefined pressure levels can be used here that are also used in the determination of the system compressibility value.

In this respect, the method in accordance with the invention for determining a system compressibility value in accordance with the first aspect of the invention is preferably used for determining the system compressibility value that is taken into account within the framework of the determination of the air proportion and/or of the air quantity in accordance with the second aspect.

The present invention furthermore comprises a membrane pump drive having a pressure sensor and having a control, with the control having a function for carrying out a method in accordance with the invention for determining an air proportion and/or an air quantity in accordance with the second aspect of the present invention. The control in this respect preferably carries out the method in accordance with the invention in an automated manner, in particular during the ongoing pump operation. The air proportion hereby determined and/or the air quantity hereby determined can in this respect in particular be taken into account in the balancing of the fluid conveyed by the membrane pump.

The membrane pump drive preferably has a coupling surface to which a pump cassette can be coupled. The membrane pump drive further preferably has a sensor for determining an operating parameter value, in particular a sensor for determining a pump drive position.

The membrane pump drive in accordance with the invention is preferably designed in this respect such as has already been presented above with respect to the method in accordance with the invention in accordance with the first aspect of the present invention.

The control of the membrane pump drive in accordance with the invention particularly preferably has both a function for carrying out a method for determining a system compressibility value in accordance with the first aspect and a function for determining an air proportion and/or an air quantity in the medical fluid conveyed by the membrane pump drive in accordance with the second aspect of the present invention.

The present invention furthermore comprises a blood treatment machine, in particular a dialysis machine, in particular a peritoneal dialysis machine, having a membrane pump drive in accordance with the first and/or second aspects.

The blood treatment machine preferably has a pump cassette receiver and/or an air cushion for pressing the pump cassette toward a coupling surface of the membrane pump drive.

BRIEF DESCRIPTION OF THE DRAWINGS

Preferred embodiments of the present invention will now be presented in more detail with reference to Figures and embodiment examples.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
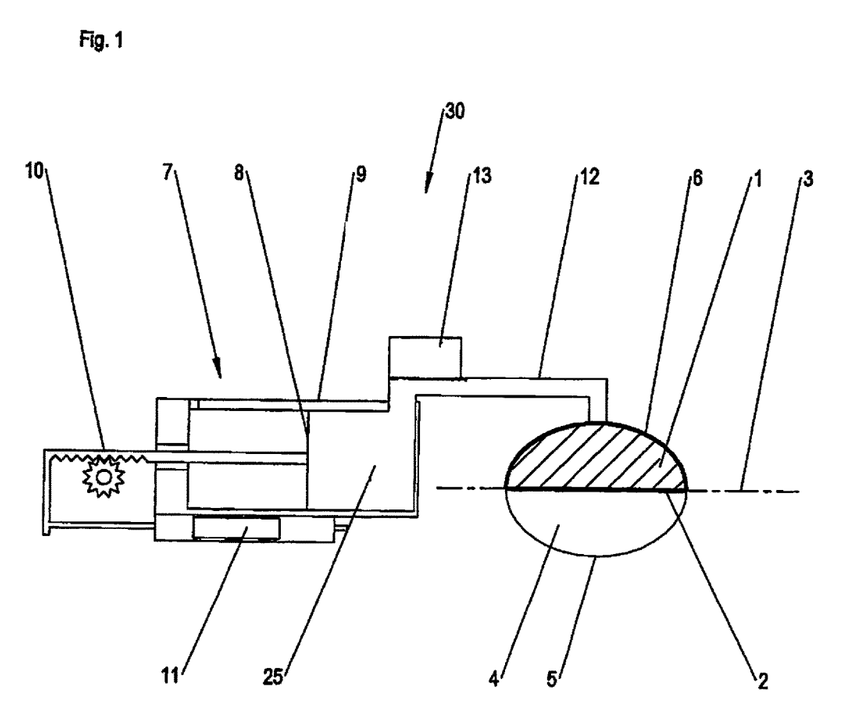
FIG. 1: a schematic representation of a membrane pump drive in accordance with the invention with a coupled pump chamber.

FIG. 1 shows an embodiment of a membrane pump drive 30 in accordance with the invention for a pumping of a medical fluid through the pump chamber 4 that is couplable to the membrane pump drive.

The membrane pump drive has a drive chamber 1 at which a flexible membrane 2 is arranged. The flexible membrane 2 is arranged in a coupling surface 3 of the membrane pump drive such that a membrane, not recognizable in FIG. 1, of the pump chamber 4 can be coupled to the membrane 2 of the drive chamber such that it follows the movements of the membrane 2 of the drive chamber. The volume of the pump chamber 4 can therefore be varied by a movement of the membrane 2 out of or into the drive chamber 1. Fluid can be pumped by the pump chamber 4 by moving the membrane 2 by the corresponding switching of valves, not shown in any more detail in FIG. 1, that control the inflow or outflow to or from the pump chamber 4.

The pump chamber 4 is in this respect typically part of a pump cassette not shown in any more detail in FIG. 1 that preferably represents a disposable. In this respect, the pump chamber is typically formed by a corresponding shaping of a hard part of the pump cassette that is covered by a flexible film forming the membrane of the pump chamber.

The present invention would, however, also be usable in the same way for membrane pumps in which the drive chamber and the pump chamber are fixedly connected to one another or are integrated in a common pumping apparatus.

In the embodiment shown in FIG. 1 it is in this respect a piston membrane pump that has a piston-in-cylinder unit 7 that is in hydraulic communication with the drive chamber 6 via the hydraulic line 12. The piston-in-cylinder unit 7 is in this respect driven by a drive 10 that acts on the piston 8 of the piston-in-cylinder unit 7 and moves it in the cylinder 9. The distance the piston 8 is traveled in the cylinder 9 is detected or measured by a length sensor 11 associated with the piston-in-cylinder unit 7.

The pressure side 25 of the piston-in-cylinder unit 7 is in this respect in fluid communication with the drive chamber 1 via the fluid line 12, with the pressure side 25, the fluid line 12 and the drive chamber 1 being filled with hydraulic fluid. The adjustment movement of the piston 8 is hereby transmitted to the membrane 2 of the drive chamber 1. The membrane 2 of the drive chamber 1 is therefore arched convexly outwardly or is pulled concavely into the inner space of the drive chamber on a corresponding change of the hydraulic volume of the piston-in-cylinder unit 7 by moving the piston 8.

The volume change of the drive chamber 1 required for the fluid conveying in the pump chamber 4 is accordingly brought about by actuating the piston-in-cylinder unit 7. The hydraulic fluid is pressed into or sucked out of the drive chamber 1 by actuating the piston 8. The membrane 2 is hereby actuated whose movement is transmitted onto the pump chamber 5 and varies its volume.

The membrane pump drive furthermore has a pressure sensor 13 via which the pressure of the hydraulic fluid in the hydraulic system and thus the pressure in the drive chamber 1 can be measured. The pressure prevailing in the drive chamber 1 in this respect corresponds—with the exception of a possible counter-pressure of the membrane 2—to the counter-pressure prevailing in the pump chamber 4 such that the pressure in the pump chamber 4 can also simultaneously be determined via the pressure sensor 13.

The membrane pump drive furthermore has a control, not shown, that is connected to the length sensor 11 and to the pressure sensor 13 and evaluates the measured signals. The control furthermore controls the drive 10 of the membrane pump drive and the valves for controlling the fluid flow into and out of the pump chamber 4.

Such a piston membrane pump has the advantage that it conveys fluid with a very exact quantity, with the totally conveyed quantity being able to be precisely balanced since the pump volume corresponds to the stroke volume of the piston-in-cylinder unit 7 and can be exactly measured by the length sensor 11.

The control of the membrane pump drive of the present invention in this respect first has a function in accordance with the second aspect of the present invention by which an air proportion and/or an air quantity in the fluid conveyed by the membrane pump can be determined. It can be prevented by this function that air bubbles that are present in the pump chamber 4 falsify the balancing of the fluid conveyed through the air chamber 4.

A measurement phase that can be interposed between the pumping process with every stroke is provided for determining the air proportion or the air quantity. First, in this respect, fluid is sucked into the pump chamber 4 by moving the membrane 2 in accordance with the usual pumping process. The cut-off valves of the pump chamber 4 are thereupon closed such that a closed fluid volume results and a first, predefined pressure level $p_a$ is moved to and the associated position of the piston 8 is determined by actuating the drive 10. A second pressure level $p_e$ is thereupon in turn traveled to and the associated position of the piston 8 is likewise determined by actuating the drive 10. If the fluid enclosed in the pump chamber 4 has a certain gas proportion, it is compressed by the pressure increase, which corresponds to a corresponding change of the volume of the pump chamber 4. This volume difference can be determined by the positions of the piston 9 present at the starting pressure and at the end pressure.

The control calculates the air quantity contained in the pump chamber from the values thus acquired, i.e. the air volume $V_{at}$ contained there at atmospheric pressure. For this purpose, the control assumes Boyle's law that reads for an isothermal state change, i.e. while neglecting a temperature change:

$$p \times V = \text{constant}.$$

Starting from this, different states of the measurement phase can be equated to:

$$V_{at} \times p_{at} = V_a \times p_e = V_e \times P_e.$$

While observing the relationship that the difference volume $V_{diff}$ is determined by the difference of the starting volume and of the end volume, that is $V_{diff} = V_a - V_e$, the actual gas volume at atmospheric pressure $V_{at}$ can be acquired therefrom:

$$V_{at} = \frac{V_{diff}}{\left(\frac{p_{at}}{p_a} - \frac{p_{at}}{p_a + p_{diff}}\right)}$$

Depending on the specifically used pump method, it must be taken into account with this formula that the pressure measured on the hydraulic side of the membrane pump via the pressure sensor 13 may not exactly correspond to the pressure in the pump chamber 4, but differs by a specific value from this pressure due to the tension of the membrane 2. In a first variant of the method, the determination of the air proportion can, however, take place with a non-deflected membrane 2 so that the influence of the membrane can be neglected. In a second variant, the starting pressure $p_a$ can in contrast be corrected by a difference pressure $p_{mem}$ due to the membrane between the hydraulic side and the pump side. It can be stored in the control, for example. It is hereby possible to carry out the determination of the air proportion while the membrane 2 has been drawn very far into or completely into the drive chamber 1 such that the complete pump volume is utilized. The differential pressure $p_{mem}$ between the hydraulic side and the pump side due to the membrane can in this respect be determined in the activation phase. Depending on the ratio between the pressures on the hydraulic side and the differential pressure $p_{mem}$ due to the membrane and the required precision, the differential pressure $p_{mem}$ can optionally also be neglected, however.

The volume difference entering into the above formula is determined by the distance of the piston $S_{diff}$ covered on the compression from the pressure level $p_a$ to the pressure level $p_e$, and its area $A_K$.

However, it must be taken into account in this respect that the movement of the piston 8 on the pressure change from $p_a$ to $p_e$ is not exclusively due to the air volume in the pump chamber 4. For the membrane pump drive itself also has a certain yielding or system compressibility under pressure changes. Factors are in this respect in particular the air that can collect in the hydraulic system and a certain flexibility of the hydraulic line 12. The piston 8 would therefore move by a certain distance $S_0$ solely due to this system compressibility on a pressure change from $p_a$ to $p_e$ even if no air at all were contained in the pump chamber 4 and the latter were thus non-compressible.

The actual volume $V_{at}$ of the air contained in the pump chamber 4 thus results while taking account of the system compressibility value $S_0$ characterizing the system compressibility.

$$V_{at} = \frac{(S_{diff} - S_0) \cdot A_k}{\left(\frac{p_{at}}{p_a} - \frac{p_{at}}{p_a + p_{diff}}\right)}$$

Since, in accordance with the second aspect of the present invention, two previously fixed pressure levels $p_a$ and $p_e$ are actively traveled to on the determination of the air volume in the pump chamber 4, the system compressibility value $S_0$ characterizing the system compressibility can be determined exactly for this pressure change. Inaccuracies that resulted in accordance with the prior art due to the use of the pressure level obtained by gravity filling as the starting pressure level $p_a$ are hereby avoided.

The control of the membrane pump drive in accordance with the invention in this respect preferably has a second function via which the system compressibility value $S_0$ can be determined. The first and second pressure levels $p_a$ and $p_e$ are also moved to, for example in the activation phase, for this purpose and the corresponding positions of the piston 8 are detected. In order in this respect only to take effects into consideration that are due to the system compressibility of the membrane pump drive and not for instance to the compressibility of the components coupled to the membrane pump drive, the determination takes place in a state of the membrane pump drive in which the membrane 2 is supported at a rigid surface. This can be achieved, for example, in that the determination of the system compressibility value takes place in a pressure range in which the membrane 2 has been deflected to a maximum outwardly or inwardly.

The determination of the system compressibility value can in this respect take place both with a pump cassette coupled to the coupling surface 3 of the membrane pump drive and without a coupled pump cassette.

Figure 2:
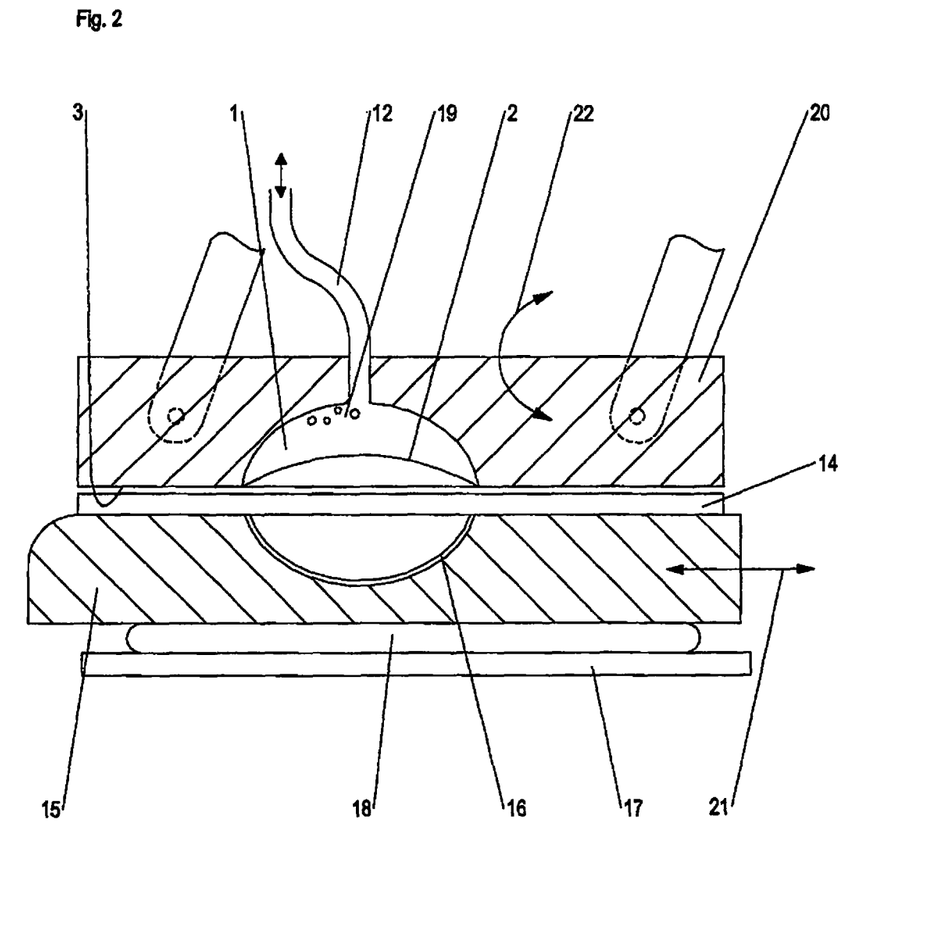
FIG. 2: a section through the coupling region of a membrane pump drive in accordance with the invention with a coupled pump cassette.

The mechanical design of an embodiment of a membrane pump drive in accordance with the invention to which a pump cassette can be coupled is in this respect shown in more detail in FIG. 2. The membrane pump drive has a machine block 20 at which the coupling surface 3 is arranged for coupling the pump cassette 14. The drive chamber 1 provided with the flexible membrane 2 is in this respect let into the coupling surface 3 and is in hydraulic communication with the piston-in-cylinder unit 7, not shown in any more detail here, via the hydraulic line 12 with fluid 19.

The pump cassette 14 is in this respect inserted into a pump cassette receiver 15 for coupling to the coupling surface 3 such that the rear side of the pump cassette is supported at a receiving surface of the pump cassette receiver 15. The receiving surface in this respect has a corresponding spherically shaped cut-out for this purpose in the region of the pump chamber 4 that is designed as a bulge of the rear side of the pump cassette.

After the insertion of the cassette 14, the cassette receiver 15 is pressed toward the coupling surface 3 via an air cushion 18 that is arranged at the rear side and that is in turn supported at a device wall 17. For this purpose, the air cushion is acted on by a corresponding operating pressure that can be, for example, between 1,500 and 2,500 mbar.

In the embodiment, the pump cassette receiver 15 is designed as a drawer that can be moved in and out in the direction 21 to insert a cassette. The machine block 20 can furthermore be placed onto the pump cassette 14 in the direction of movement 22. After the pushing in of the drawer 15 and the placing on of the machine block 20, the air cushion 18 is then pressurized to achieve a secure coupling of the pump cassette 14 to the coupling surface 3.

Alternatively to the constructive design shown in FIG. 2, the pump cassette receiver 15 could, however, also be designed as a door, for example, that is opened for inserting the pump cassette 14 and is closed for placing the pump cassette 14 at the coupling surface. The air cushion 18 would be integrated into the door in this case.

Figure 3:
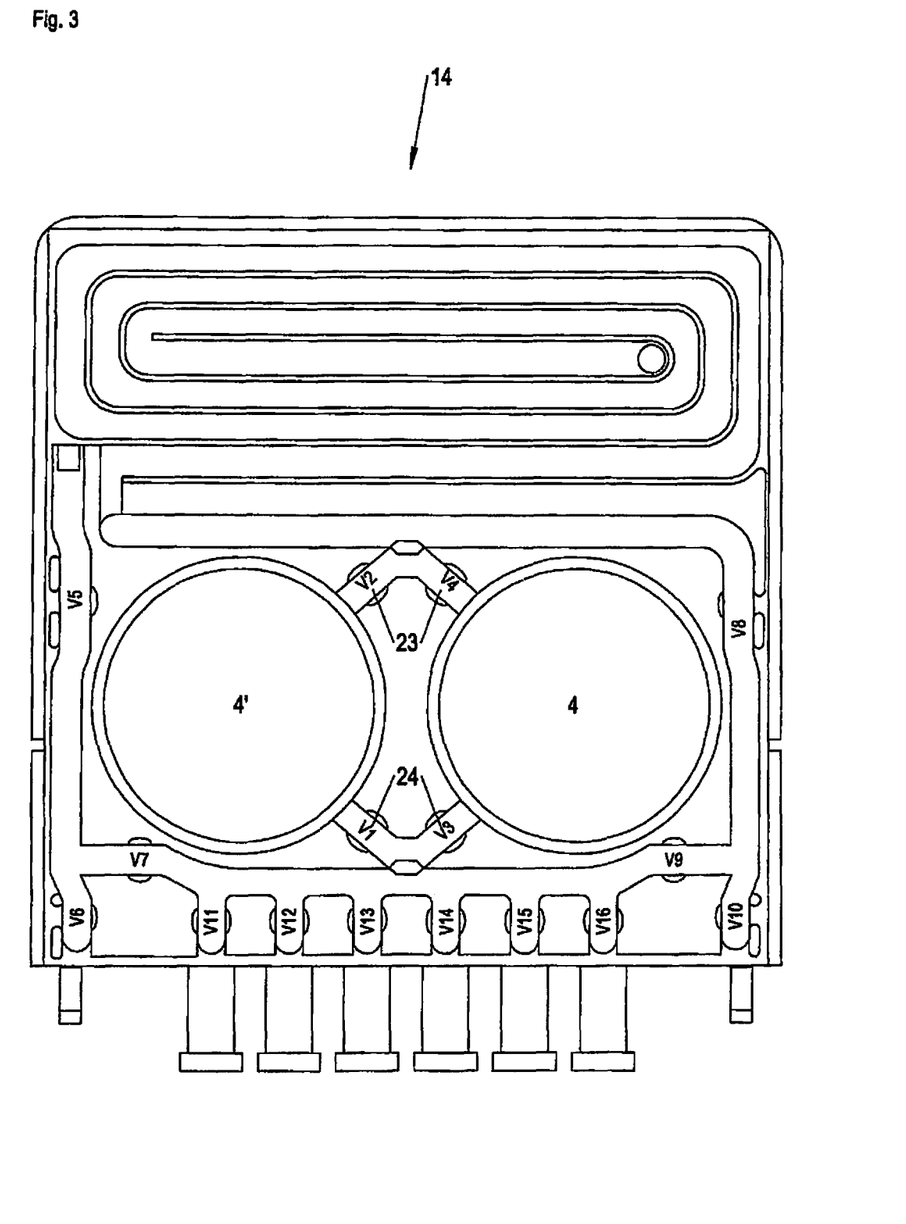
FIG. 3: am embodiment of a pump cassette such as can be coupled to a membrane pump drive in accordance with the invention.

In this respect, an embodiment of a pump cassette 14 is shown in FIG. 3 that has two pump chambers 4 and 4'. The pump cassette in this respect comprises a hard part into which the fluid-conducting channels and the pump chambers are let and is covered by a flexible film with respect to the coupling surface. The pump cassette in this respect inter alia has the valves 23 and 24 via which the fluid flow into and out of the pump chambers 4 and 4' can be controlled. The valves are in this respect likewise actuated via actuators arranged in the machine block 20.

The determination in accordance with the invention of the system compressibility value in this respect preferably takes place in the activation phase of the membrane pump, but can in this respect be carried out both with an inserted pump cassette and without an inserted pump cassette.

If the determination is carried out as long as no pump cassette 14 was inserted, the membrane is supported on the receiving surface 16 of the pump cassette receiver 15 during the carrying out of the measurements. If in contrast the determination is carried out with an inserted pump cassette, the membrane 2 is supported on the rear wall 5 of the pump chamber 4 and thus on the hard part of the pump cassette. With an inserted pump cassette, at least one of the valves that control the fluid flows into and out of the respective pump chamber has to be open for this purpose. The determination of the system compressibility value in this respect advantageously takes place before the filling of the pump cassette with fluid or while the pump chamber is in communication, for example, with the dialysis bag or the drainage back via the fluid connections.

The fact that the membrane contacts the receiving surface 16 of the pump cassette receiver or the rear wall of the pump chamber during the measurement phase is achieved by correspondingly high pressure levels $p_a$ and $p_e$ that provide a complete deflection of the membrane during the measurement process. The tension of the membrane 2 is in this respect already completely overcome by the reaching of the first pressure level $p_a$. On the pressure increase to the second pressure level $p_e$, the membrane is then supported on a rigid counter-surface such that the membrane or components coupled thereto has/have no influence on the determination of the system compressibility value.

Since the tension of the membrane 2 is overcome at a pressure level of approximately 50 mbar, a suitable first pressure level lies at approximately 200 mbar; a suitable second pressure level at approximately 300 mbar.

In this respect, the same pressure levels are preferably used for determining the system compressibility value that are also used for determining the air volume in the fluid conveyed by the pump. The distance the piston 8 covers on the pressure increase from $p_a$ to $p_e$ can hereby simply be used as the system compressibility value $S_0$. The system compressibility value $S_0$ thus results as the difference from the position values of the membrane pump drive determined from the pressure levels $p_a$ and $p_e$.

As already presented above, the air content of the hydraulic fluid and the stiffness of the hydraulic hoses represent the main influence factors on the system compressibility. However, mechanical tolerances and a deformation of the mechanical components can also result in a certain yielding of the system and thus in an increase in the system compressibility value.

The determination of the system compressibility value therefore preferably takes place after the air cushion 18 has been filled to the operating pressure such that the pump cassette receiver 15 is pressed toward the coupling surface 3. The influence the clearance of the pump cassette receiver and a possible mechanical deformation of the involved mechanical components could have on the determination of the system compressibility value is hereby reduced. In addition, the determination of the system compressibility value hereby takes place in the same situation that is then also present in the determination of the air proportion during the pump operation. The pump cassette receiver is in this respect pressed toward the coupling surface via the air cushion 18 independently of whether the determination of the system compressibility value is carried with or without an inserted pump cassette.

To the extent that the system compressibility value is in this respect influenced by the operating pressure of the air cushion, the regulation tolerance of the internal air cushion pressure can be restricted for a further increase in the accuracy.

In accordance with the above-described variants, the determination of the system compressibility value takes place at excess pressure such that the membrane 2 arches outwardly out of the drive chamber 1 and is supported on an outwardly arranged counter-surface.

The determination in accordance with the invention of the system compressibility value can, however, also be reached at vacuum levels. In this case, the vacuum levels are selected such that the membrane 2 is supported on the rear wall 6 of the drive chamber 1. A suitable first pressure level is in this respect approximately −200 mbar; a suitable second pressure level approximately −300 mbar. The suitable vacuum levels thus correspond by amount to the suitable excess pressure levels.

In the event that the determination of the system compressibility value takes place at vacuum levels $p_a$ and $p_e$, work is preferably also carried out in accordance with the above-shown second aspect with vacuum levels $p_a$ and $p_e$ to determine the air volume in the fluid pumped through the pump chamber.

If work is carried out in this respect with vacuum levels on the determination of the system compressibility value, the mechanical properties of the design of the air cushion, the pump cassette receiver and the machine block do not affect the measurement.

Provision can furthermore be made in accordance with the invention respectively to determine a system compressibility value with excess pressure levels and with vacuum levels. The mechanical properties of the design of the air cushion, the pump cassette mount and the machine block can be determined by the use of both methods and they can be separated from the properties due to the hydraulic system.

The determination of the system compressibility value at vacuum can likewise take place with or without an inserted pump cassette. If it takes place with an inserted pump cassette, the valves with which the pump chamber communicates with further components should be open.

The system compressibility value determined in accordance with the invention can in this respect, on the one hand, enter into the determination of the air volume of the conveyed medical fluid as shown above. It in this respect allows a more exact balancing of the fluids moved through the membrane pump since the air volume in the pumped fluids can be determined more precisely.

The determination of the system compressibility value can furthermore be used to verify the quality of the degassing of the hydraulic system. In this respect, for example, as soon as the system compressibility value exceeds a certain threshold, a degassing of the hydraulic system can be carried out or its necessity can be displayed.

The membrane pump drive in accordance with the invention is preferably used in a blood treatment device for pumping medical fluids, in particular for pumping blood or dialyzate. The membrane drive pump in accordance with the invention is in this respect particularly preferably used in a dialysis machine, with the membrane pump being used for pumping the dialyzate into the abdomen of the patient or for removing the dialyzate from the abdomen of the patient.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method of determining a system compressibility value of a medical membrane pump drive of a medical device, the membrane pump drive including a membrane, a coupling surface for coupling a pump cassette to the medical device, a drive chamber arranged in the coupling surface, said drive chamber being closed by said membrane, a piston-in-cylinder unit including a piston movable in a cylinder, the cylinder connected to the drive chamber for adjusting a pressure in the drive chamber by moving the piston, and a pressure sensor for determining the pressure in the drive chamber, said membrane being deflected outwardly out of the drive chamber by excess pressure in the drive chamber and being deflected inwardly into the drive chamber by negative pressure in the drive chamber, the membrane being deformable from a flat configuration inwardly to a first maximum deflection where the membrane contacts a first rigid surface of the medical device and outwardly to a second maximum deflection where the membrane contacts a second rigid surface of the medical device or the pump cassette coupled to the medical device, the method comprising:
   moving the piston of the piston-in-cylinder unit to produce a first pressure level in the drive chamber, said first pressure level exceeding a maximum counter-pressure of the membrane such that the membrane is deflected inwardly to the first maximum deflection in contact with the first rigid surface or is deflected outwardly to the second maximum deflection in contact with the second rigid surface;
   detecting a first position of the piston of the piston-in-cylinder unit of the membrane pump drive associated with the first pressure level;
   moving the piston of the piston-in-cylinder unit to produce a second pressure level in the drive chamber, the second pressure level exceeding the maximum counter-pressure of the membrane such that the membrane is still deflected inwardly to the first maximum deflection in contact with the first rigid surface or is still deflected outwardly to the second maximum deflection in contact with the second rigid surface;
   detecting a second position of the piston of the piston-in-cylinder unit of the membrane pump drive associated with the second pressure level; and
   determining the system compressibility value on the basis of the first and second positions of said piston.

2. The method in accordance with claim 1, wherein the medical device includes a pump cassette receiver having a receiving surface supporting a rear side of the pump cassette when a front side of the pump cassette is coupled to the coupling surface, the method further comprising a step of coupling the pump cassette to the membrane pump drive, with the cassette being received in the pump cassette receiver in a coupled state; wherein the step of coupling the pump cassette to the membrane pump drive is performed after the step of determining the system compressibility value, and wherein the second rigid surface in contact with the membrane during the determination of the system compressibility value is the receiving surface of the pump cassette receiver.

3. The method in accordance with claim 1, wherein the pump cassette includes a pump chamber, the method further comprising a step of coupling the pump cassette to the membrane pump drive; wherein the step of determining the system compressibility value is performed after the step of coupling the pump cassette to the membrane pump drive and wherein the membrane is completely pressed into the pump chamber of the pump cassette and being supported at a rear wall of the pump chamber during the determining of the system compressibility value, such that the second rigid surface is formed by the rear wall of the pump chamber.

4. The method is accordance with claim 1, wherein the system compressibility value is determined at a negative pressure, with the membrane being completely drawn into the drive chamber of the membrane pump drive and contacting a rear wall of the drive chamber during the determining of the system compressibility value, such that the first rigid surface is formed by the rear wall of the drive chamber.

5. The method in accordance with claim 1, wherein the medical device includes an air cushion via which, in normal operation, the pump cassette is pressed toward the coupling surface of the membrane pump drive from its rear side, wherein the method further comprises the step of filling the air cushion to an operating pressure before determining the system compressibility value.

6. The method in accordance with claim 1, wherein a difference between the first and second pressure levels is greater than 5 mbar and less than 500 mbar.

7. The method in accordance with claim 1, wherein a first system compressibility value is determined at negative pressure values and a second system compressibility value is determined at excess pressure values.

8. The method in accordance with claim 1, wherein the system compressibility value is determined in dependence on a difference between the first position and the second position of the piston of the piston-in-cylinder unit.

9. The method in accordance with claim 1, wherein the first position and the second position of the piston of the piston-in-cylinder unit is determined using a length sensor.

10. The method of claim 9, wherein the piston-in-cylinder unit and the drive chamber are filled with hydraulic fluid.

11. The method in accordance with claim 1, comprising the further steps of:
   coupling the membrane pump cassette to the membrane pump drive;
   pumping a fluid through a pump chamber of the membrane pump cassette by operating the membrane pump drive;
   moving the piston to produce a third pressure level and a fourth pressure level in the drive chamber;

detecting a third position and a fourth position of the piston associated with the third and the fourth pressure levels, respectively; and determining at least one of an air proportion and an air quantity in the fluid pumped through the pump chamber of the membrane pump cassette on the basis of the third and fourth positions of the piston.

12. The method in accordance with claim 11, wherein the system compressibility value of the membrane pump drive is taken into account in the determination of the at least one of the air proportion and the air quantity; and wherein the third pressure level is equal to the first pressure level and the fourth pressure level is equal to the second pressure level.

13. The method of claim 1, wherein a transmission of pressure onto the membrane takes place hydraulically.

14. A membrane pump drive of a medical device comprising:
- a coupling surface for coupling a pump cassette to the membrane pump drive;
- a drive chamber arranged in the coupling surface, said drive chamber being closed by the membrane of said membrane pump drive, said membrane being deflected outwardly out of the drive chamber by excess pressure in the drive chamber and being deflected inwardly into the drive chamber by negative pressure in the drive chamber, the membrane being deformable from a flat configuration inwardly to a first maximum deflection where the membrane contacts a first rigid surface of the medical device and outwardly to a second maximum deflection where the membrane contacts a second rigid surface of the medical device or the pump cassette coupled to the medical device;
- a piston-in-cylinder unit including a piston movable in a cylinder, the cylinder connected to the drive chamber for adjusting a pressure in the drive chamber by moving the piston;
- a pressure sensor for determining the pressure in the drive chamber; and
- a controller, said controller being configured to carry out a method of determining a system compressibility value, the method including the steps of moving the piston of the piston-in-cylinder to produce a first pressure level in the drive chamber, wherein the first pressure level exceeds a maximum counter-pressure of the membrane such that the membrane is deflected inwardly to the first maximum deflection in contact with the first rigid surface or is deflected outwardly to the second maximum deflection in contact with the second rigid surface;

detecting a first position of the piston of the piston-in-cylinder unit of the membrane pump drive associated with the first pressure level;

moving the piston of the piston-in-cylinder unit to produce a second pressure level in the drive chamber, the second pressure level exceeding the maximum counter-pressure of the membrane such that the membrane is still deflected inwardly to the first maximum deflection in contact with the first rigid surface or is still deflected outwardly to the second maximum deflection in contact with the second rigid surface;

detecting a second position of the piston of the piston-in-cylinder unit of the membrane pump drive associated with the second pressure level; and determining the system compressibility value on the basis of the first and second positions of the piston.

15. A blood treatment machine having a membrane pump drive in accordance with claim 14.

16. The blood treatment machine of claim 15, wherein the blood treatment machine is a dialysis machine.

17. The blood treatment machine of claim 15, further comprising a pump cassette receiver and an air cushion for pressing the pump cassette to the coupling surface of the membrane pump drive.

* * * * *